(12) United States Patent
Fitzgerald et al.

(10) Patent No.: US 8,057,503 B2
(45) Date of Patent: Nov. 15, 2011

(54) BLOOD VESSEL OCCLUDER AND METHOD OF USE

(75) Inventors: Timothy L. Fitzgerald, Grand Rapids, MI (US); Michael P. Ashbrook, Grand Rapids, MI (US); John D. Hall, Grand Rapids, MI (US); Kenneth R. Jonkman, Marne, MI (US); Christopher C. Knowlton, Grand Rapids, MI (US)

(73) Assignee: Trinity Health-Michigan, Grand Rapids, MI (US)

( * ) Notice: Subject to any disclaimer, the term of this patent is extended or adjusted under 35 U.S.C. 154(b) by 700 days.

(21) Appl. No.: 12/019,183

(22) Filed: Jan. 24, 2008

(65) Prior Publication Data

US 2008/0183203 A1 Jul. 31, 2008

Related U.S. Application Data

(60) Provisional application No. 60/897,409, filed on Jan. 25, 2007.

(51) Int. Cl.
*A61M 29/00* (2006.01)
(52) U.S. Cl. .................................. 606/198; 606/191
(58) Field of Classification Search .............. 606/108, 606/194, 198, 200, 191; 604/104, 96, 3.09
See application file for complete search history.

(56) References Cited

U.S. PATENT DOCUMENTS

| 4,921,484 | A | * | 5/1990 | Hillstead ................. 604/104 |
| 5,034,001 | A | | 7/1991 | Garrison et al. |
| 5,792,156 | A | | 8/1998 | Perouse |
| 5,800,522 | A | | 9/1998 | Campbell et al. |
| 6,113,613 | A | | 9/2000 | Spaulding |
| 6,468,291 | B2 | * | 10/2002 | Bates et al. ................. 606/200 |
| 6,635,068 | B1 | | 10/2003 | Dubrul et al. |
| 6,966,923 | B2 | | 11/2005 | Gittings |
| 2006/0041269 | A1 | | 2/2006 | Horrigan |
| 2007/0299424 | A1 | | 12/2007 | Cumming et al. |

FOREIGN PATENT DOCUMENTS

EP 0518704 A1 6/1991
EP 0472731 A1 3/1992

OTHER PUBLICATIONS

How To Do It By Smart Canula, Cannulation, www.smartcanula.com, No. 0608, 7 pages.

* cited by examiner

*Primary Examiner* — Tuan Nguyen
(74) *Attorney, Agent, or Firm* — Dickinson Wright PLLC

(57) ABSTRACT

A vessel occluder is disposed inside a principal blood vessel for occluding tributary blood vessels inside the principal blood vessel while still allowing blood to flow through the principal vessel. The vessel occluder includes a support structure and associated membrane that can be collapsed for insertion into the principal vessel. Once inserted at the desired location the support structure is allowed to expand, forcing the membrane to contact the inner walls of the vessel with sufficient force to occlude the openings of the tributary vessels.

10 Claims, 4 Drawing Sheets

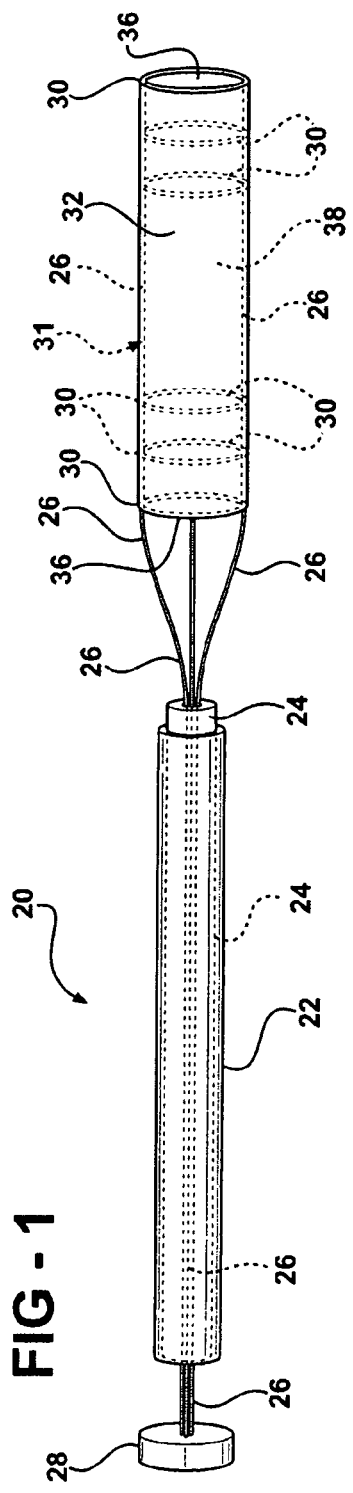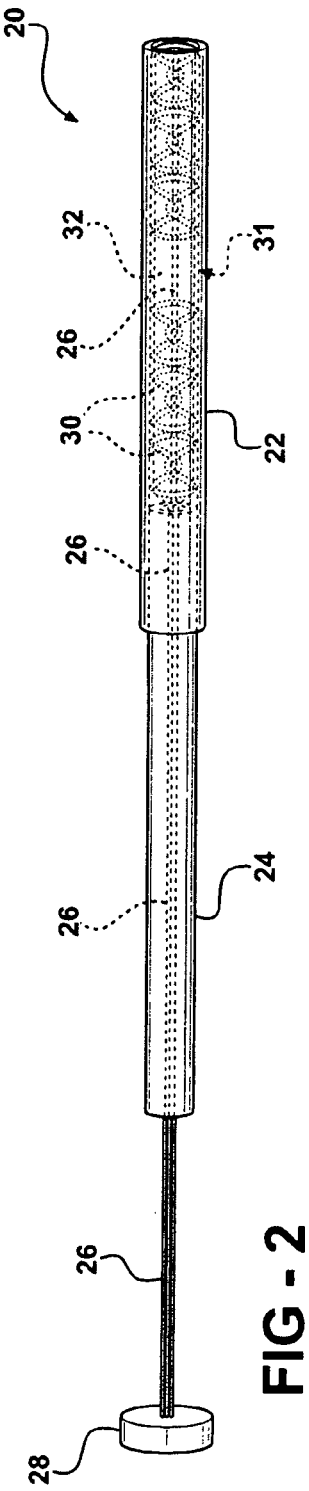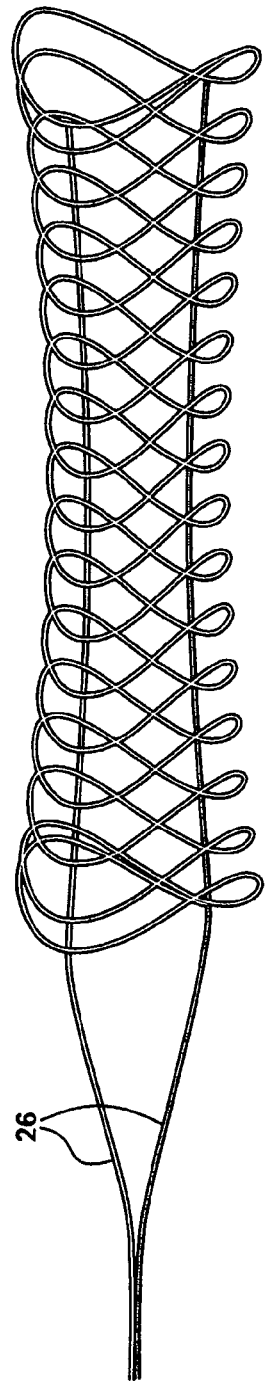

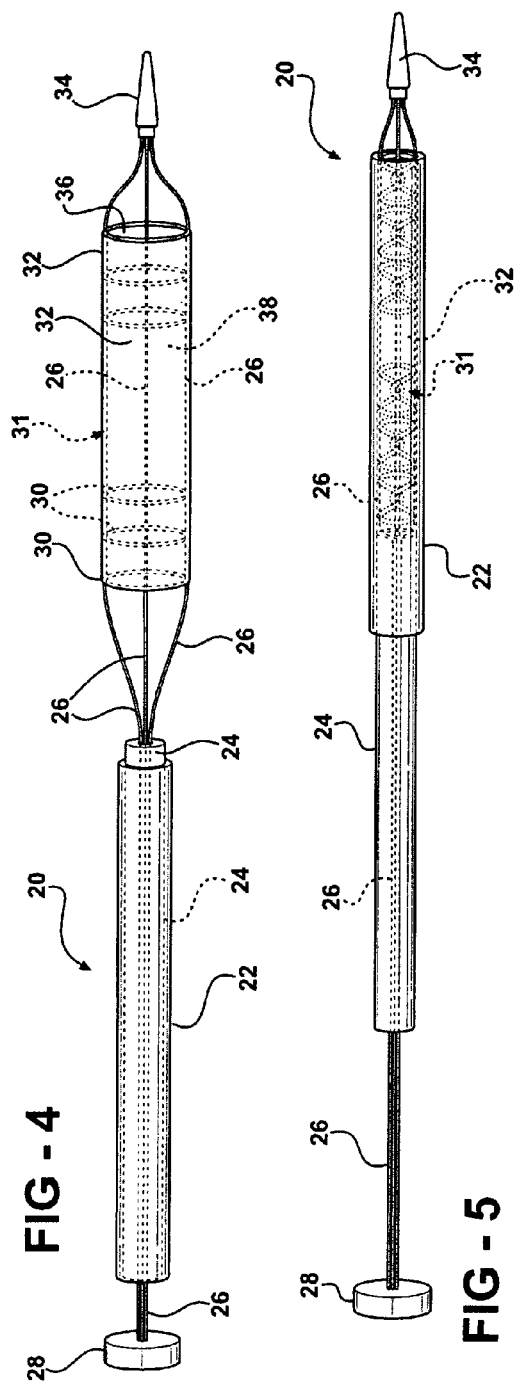

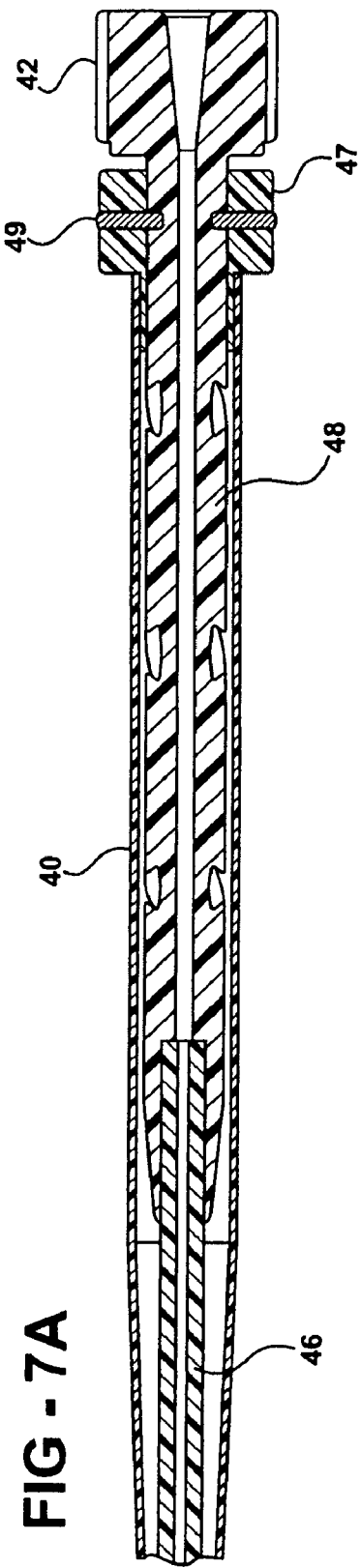
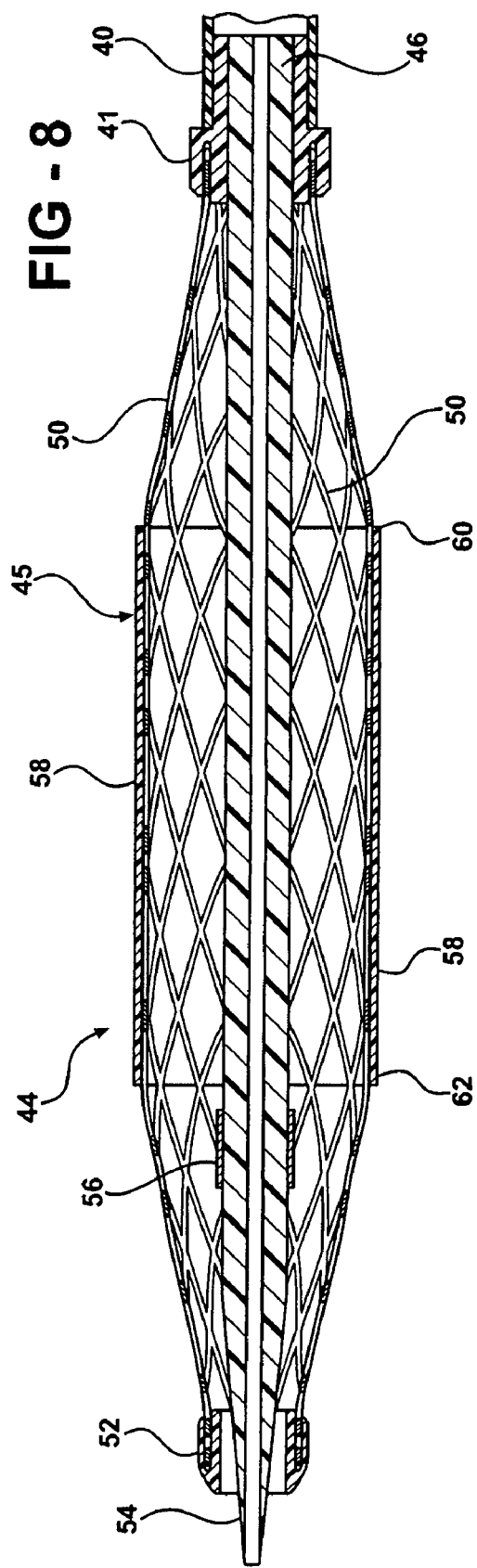

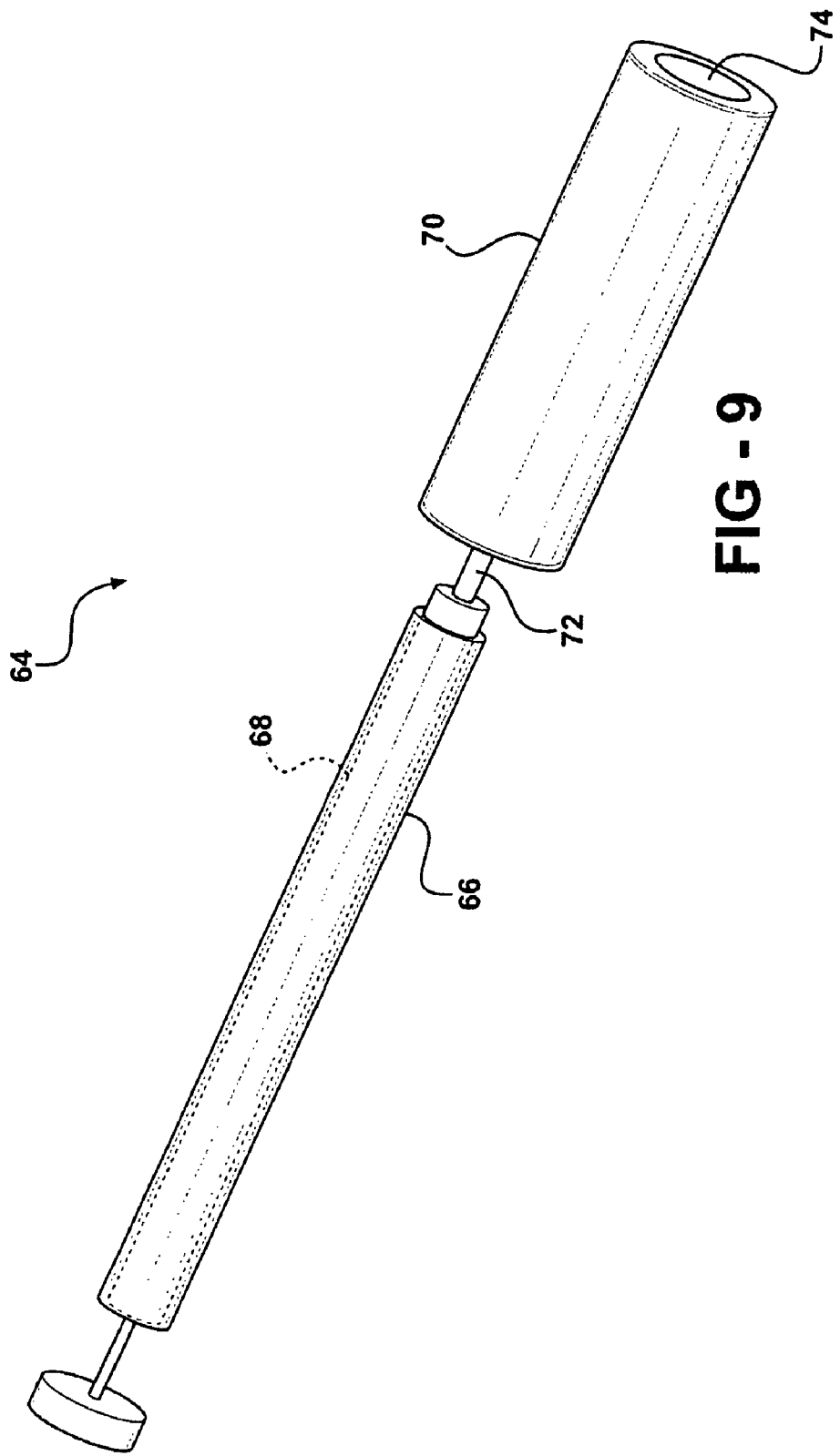

BLOOD VESSEL OCCLUDER AND METHOD OF USE

The present invention claims priority from U.S. provisional application Ser. No. 60/897,409, filed on Jan. 25, 2007, and entitled "PROGRADE PRECLUSION VASCULAR OCCLUSION DEVICE AND METHOD OF USE"; the entire disclosure of this provisional application is incorporated herein by reference.

FIELD OF THE INVENTION

The present invention relates generally to the field of catheters and cannulae. More specifically, the present invention relates to devices and techniques for temporarily blocking blood flow from a vessel into an adjacent area.

BACKGROUND OF THE INVENTION

Medical devices for treating narrowed and occluded blood vessels are well known in the art. When treating a narrowed or occluded blood vessel, it is often necessary to provide support to the vessel while simultaneously allowing for the perfusion of blood. Collapsible and expandable stents and stent delivery systems have been used for this purpose. A stent delivery system typically inserts a stent into the lumen of an anatomical vessel to keep a previously blocked passageway open while simultaneously allowing blood to perfuse through the stent. An example of such a system is disclosed in the U.S. Pat. No. 6,966,923 (the '923 patent) to Gittings.

The '923 patent discloses a collapsible and expandable support. The support is collapsed and disposed within a sheath, being axially moveable within the sheath. The sheath is inserted into the lumen of a blood vessel, and an external force applied to the support axially moves the support outwardly of the sheath into the lumen of the blood vessel causing the support to expand. The support expands outwardly against the interior walls of the blood vessel, unblocking and supporting the blood vessel while allowing for the perfusion of fluid. The collapsible and expandable support disclosed in the '923 patent remains in the lumen of the blood vessel, supporting the passageway, while the sheath is removed.

Additional collapsible and expandable stents are disclosed in the prior art which include a guidewire attached to the collapsible and expandable support. An example of such a system is disclosed in the U.S. Pat. No. 5,034,001 to Garrison et al. (the '001 patent). The '001 patent discloses a sheath and a guidewire being axially moveable within the sheath. An expandable and collapsible support is disposed on the guidewire with the support being axially moveable inwardly of the sheath to collapse the support and is axially moveable outwardly of the sheath to expand the support. The '001 device does not use an expandable cage to block tributary vessels.

In addition to stents being collapsible within a sheath, the prior art also discloses stents being collapsible without a sheath. The U.S. Pat. No. 4,921,484 to Hillstead discloses a support end disposed on a guidewire. A mechanism for moving the proximal support end axially along the guidewire opposite the distal support end collapses the support. The guidewire and support are inserted into the lumen of a blood vessel and a mechanism for moving the proximal support end axially along the guidewire towards the distal support end causes the support to expand outwardly against the blood vessel, supporting the blood vessel while simultaneously allowing for the perfusion of fluid through the vessel. The Hillstead device does not use an expandable cage to block tributary vessels.

While the prior art stents support a blood vessel allowing for the perfusion of blood, it is oftentimes necessary to isolate a blood vessel during surgical repair. In such circumstances, the side branches or sections of major vessels are typically clamped to prevent retrograde or antegrade flow to or from smaller vessels that branch off of major vessels. By occluding these vessels, a clearer operating field is achieved and less blood units may be required during the procedure.

SUMMARY OF THE INVENTION

In one aspect the present invention provides a blood vessel occluder having a sheath which houses a fluid impermeable membrane attached to a flexible, expandable support. In one position, the expandable support with the attached membrane is retracted into the sheath so that an end of the sheath can be inserted into the lumen of a blood vessel. In a second position, the support with the attached membrane is pushed out of the sheath such that the support expands, causing the membrane to produce a small biasing force on the interior walls of the blood vessel to close tributary vessels. The support and membrane form a tube-shaped structure in line with the vessel lumen so that blood can continue to flow through the vessel lumen while the tributary vessels are occluded. It is to be understood that the flow occluded can be the physiological direction of flow from the tributary vessels into the principal vessel or reverse (retrograde) flow.

It will be appreciated by those skilled in the art that the present invention is particularly suited to block blood flow during a surgical procedure on a vessel or adjacent organ (i.e. liver, kidney, etc.). By isolating side branches of vessels without the necessity of tying or clamping, time in the operating room is reduced. Most importantly, the present invention allows these side branches to be occluded while still allowing blood to flow through the principal vessel.

In another aspect the present invention provides a preformed cage which supports the membrane. A dilator is associated with the cage and is used both to insert the occluder into the vessel and to extend or stretch the cage to an insertion size compatible with the lumen of a vessel. After the cage and membrane are properly positioned within the vessel the dilator is retracted somewhat to allow the cage to expand whereupon the membrane produces a small biasing force on the inner walls of the vessel sufficient to occlude blood flow from tributary vessels. Since the cage is essentially a mesh tube-shaped structure with the membrane occupying only a central span of the cage, blood continues to flow through the vessel while the membrane simultaneously occludes tributary vessels.

Still further, the present invention provides a method of occluding tributary vessels by providing a blood vessel occluder in accordance with the teaching of the present invention. The occluder is positioned in the lumen of a principal vessel such that the membrane covered support exerts a biasing force on the vessel inner walls sufficient to stop or reduce blood flow between tributary vessels and the principal vessel while still allowing the flow of blood through the lumen of the principal vessel in which membrane and support are positioned.

BRIEF DESCRIPTION OF THE DRAWINGS

The following Figures are provided to assist in the description of certain embodiments of the invention. The drawings are not necessarily to scale and like numerals indicate like parts.

FIG. 1 is a side elevational view of the occluder in one embodiment in which the support is formed of concentric, flexible rings that are shown outside the end of the outer catheter body and supporting a membrane; the support and membrane being shown in the expanded state.

FIG. 2 is the embodiment depicted in FIG. 1 with the support and membrane in the collapsed state inside the outer catheter body.

FIG. 3 is a perspective view of another support in its expanded state (without an attached membrane) which is collapsible and which can be substituted for the support shown in FIG. 1.

FIG. 4 is another version of the occluder shown in FIGS. 1 and 2, having the support shown in the expanded state, but with the addition of a dilator tip.

FIG. 5 is the occluder shown in FIG. 4 but with the support and membrane in the collapsed state.

FIG. 6 is a side elevational view of another embodiment of the invention in which a cage is shown in the expanded state.

FIG. 7 is a cross-section along line A-A of the side elevation of the embodiment shown in FIG. 6.

FIG. 7A is a cross-section of the actuator portion of the device in one embodiment.

FIG. 8 is a cross-section of the cage (detail A) shown in FIGS. 6 and 7.

FIG. 9 is a perspective view of another embodiment of the invention in which an inflatable balloon in the nature of a cuff is used to seal off tributary vessels.

DETAILED DESCRIPTION OF THE PREFERRED EMBODIMENTS

Referring now to FIG. 1 of the drawings, vessel occluder 20 is shown generally having outer catheter body 22 closely nested around inner catheter body 24. In this embodiment inner catheter body or tube 24 is provided primarily as a spacer between push/pull rod or wires 26 and the inner walls of body 22. Catheter body 22 and tube 24 are made of a flexible plastic such as a polyolefin or fluoropolymer PVC or Nylon. A knob 28 is secured to one end of wires 26. The other ends of wires 26 are either attached to or are formed into two collapsible ring structures 30 to form support structure 31. In FIG. 1 six rings 30 are shown forming support 31, with the center-most four rings 30 shown in phantom. By forming support 31, rings 30 and wires 26 provide support to membrane 32 when in the expanded state. Membrane 32 is a thin, flexible elastomeric material which is adhered to wires 26 with adhesive or can be formed over wires 26 through a dip procedure or the like. Membrane 32 is formed of any biocompatible material such as an elastomeric silicone or a polyurethane. It may be advantages to coat the surfaces of membrane 32 and other surfaces of occluder 20 with an anti-coagulation agent such as heparin to prevent blood cells from sticking thereto. All of the tissue contacting surfaces of the present invention are made of biocompatible materials. Membrane 32 will typically have a thickness of only several thousandths of an inch.

As seen in FIG. 2, by pulling knob 28, wires 26 are pulled so that support 31 collapses with membrane 32 as it is retracted into catheter body 22. Wires 26 are not attached to in the inner surfaces of inner catheter or tube 24 (and note the passage through inner catheter or tube 24 is sufficiently large to also accommodate a guide wire in some embodiments). The consolidation of the collapsed support 31 and membrane 32 abut and move tube 24 to the position shown in FIG. 2.

FIG. 3 illustrates another arrangement of wires 26 to form support 31. FIG. 3 is shown without the attachment of membrane 32 for simplicity.

In FIG. 4, occluder 20 is shown with a dilator tip 34 attached at the end of wires 26 with support 31 in the expanded state. FIG. 5 shows the position of dilator tip 34 when support 31 and membrane 32 are retracted within catheter body 22.

In use, a portion of catheter body 22 and support 31 are inserted into a vessel. Where administration is percutaneous, that version of the occluder shown in FIG. 5 having dilator tip 34 will typically be used. Using the Seldinger technique, a small incision is created using an insertion needle or device such as a trocar or the like. A guide wire is then extended into the lumen of a vessel. The dilator tip is then fed onto the guide wire and is inserted into the vessel lumen. Catheter body 22 is then urged over the guide wire which passes through inner tube 24 along side of wires 26 into the vessel in the location required. The guide wire is then removed. The dilator tip or other components of occluder 20 are preferably made of a radio-opaque material to allow visualization (imaging) so that support 31 and membrane 32 can be accurately placed at a point where tributary vessels can be occluded. Once the occluder is in the proper location, knob 28 is pushed to move support 31 and membrane 32 out of catheter body 22 whereupon support 31 pops open to expand, thereby biasing membrane 32 against the inner walls of the vessel with sufficient force to occlude or block tributary vessels. Fluid (typically blood) continues to flow through the lumen of the vessel by virtue of openings 36 and passage 38 through support 31. The outer diameter of catheter body 22 is smaller than the internal diameter of the vessel in which it resides so that it allows fluid to flow freely around it. It is to be understood that a number of materials can be used to form support 31 so long as they are flexible enough to fold into catheter body 22 and can resume a pre-tensioned, expanded configuration. One preferred material for forming support 31 is the memory metal nitinol. A nitinol support 31 will have as its retained state the fully expanded configuration shown in FIGS. 1 and 3. Stainless steel may also be suitable for forming support 31.

In the case of open surgery, it may not be necessary to have a dilator tip on the end of support 31 since it will be possible to insert the end of catheter body 22 directly into the lumen of a vessel, thus bypassing the Seldinger technique.

One of the advantages of the present invention is that to reposition support 31 (and thus membrane 32) one need only pull knob 28, thereby collapsing and retracting support 31 into catheter body 22, to reposition support 31 within the vessel.

Referring now to FIG. 6 of the drawings, another embodiment of the present invention is shown in which vessel occluder 39 has catheter body 40 with an actuator knob 42 on one end and cage assembly 44 (shown in its expanded state) on the other end. In this embodiment and referring now to FIG. 7 of the drawings, catheter body 40 houses closely nested dilator tube 46. Although not shown in the drawings, it may be desirable to use a catheter body 40 which has an integrated metal reinforcement coil or braid to reduce any tendency for the tube which comprises catheter body 40 from stretching or kinking during use. Such reinforcement coils and braids are well known to those skilled in the art. Catheter body 40 and dilator tube 46 may be formed of numerous plastics, such as polyurethane, PVC, Nylon or other materials such that catheter body 40 and dilator tube 46 are reasonably flexible. Dilator tube 46 slides easily along the inner surfaces of catheter body 40 and very little space is provided for clearance between the two. Of course, as with the previous embodiment the external diameter of catheter body 40 is sufficiently smaller than the internal diameter of the vessel in which it is to be inserted such that in use blood can continue to flow in the vessel around the catheter body.

Referring again to FIG. 7, push/pull rod or actuator 48 is shown which is attached to one end of dilator tube 46. Push/pull rod 48 is a plastic tube that can accommodate a guide wire through its center. It may be desirable in some applications to extend dilator tube 46 to the end of catheter body 40 for a direct connection to actuator knob 42. It is also desirable to provide an actuator knob 42 with the capacity to lock cage assembly 44 in either its expanded state or its collapsed state, the latter of which in this embodiment comprises a reduction in diameter of cage 45 by stretching cage 45 lengthwise. Such locking mechanisms will be apparent to those skilled in the art. In addition to a locking mechanism, it may be desirable to place indicia on push/pull rod 48, dilator tube 46 and/or catheter body 40 to provide an estimate of the extent to which cage 45 is expanded or to gauge the distance catheter body 40 has traveled.

Referring now to FIG. 7A of the drawings, the connection of push-pull rod 48 to dilator tube 46 is shown in more detail. In this view, push-pull rod is shown in the position in which cage 45 is in its collapsed (stretched) configuration. In this embodiment, annular shoulder 47 is provided having pins 49 that engage threads 51.

Referring now to FIG. 8, cage assembly 44 has cage 45 which is formed from wire strands 50 as a braided or woven structure which is pre-tensioned to form the expanded cage 45 as shown. In other words, cage 45 is in the expanded state when no forces are exerted on it. In the expanded state cage 45 has an outer diameter which is just slightly (a few thousands inch) larger than the internal diameter of the vessel into which it is to be inserted. This difference in diameter is necessary to achieve the blockage of tributary vessels by membrane 58 when cage 45 is expanded in situ. The number of strands 50 used my vary widely within two parameters: the cage must in the expanded state have sufficient biasing force to stay expanded in the vessel and the number of strands and weaving pattern should not make cage 45 a closed weave, i.e., it is the open mesh work of cage 45 which allows fluid to flow through cage 45 and thus through the lumen of the vessel into which it is inserted. One suitable material from which strands 50 may be formed is nitinol. Stainless steel may also be appropriate. With either material, it is important that the expanded state of cage 45 be imprinted on the material so that cage 45 expands when no stretching force is exerted on it. Strands 50 are anchored at one end by heat fusing or gluing the strand ends to the end of catheter body 40. In this illustration a small collar 41 is used to secure wire strands 50 in place. At the opposite end, strands 50 are secured to collar or ring 52. It may be possible to heat bond strands 50 to collar 52 or to bond using an adhesive. It also may be desirable to use a metal collar 52, perhaps made of nitinol, and use metal forming techniques for swaging collar 52 in place to hold the ends of strands 50 securely. Due to the environment in which vessel occluder is used, it is important that the ends of strands 50 remain secured by collar 41 and ring 52. Suitable braided nitinol cages of various sizes can be purchased from Secant Medical LLC of Perkasie, Pa.

Ring 52 fits closely around tapered tip 54 of dialator tube 46. As knob 42 is turned or pushed, force is exerted on dialator tube 46 via push/pull rod 48 to move tip 54 out of cage assembly 44. As tip 54 moves, along with the entire dialator tube 46, annular shoulder 56 integral with dialator tube 46, catches on ring 52. Since ring 52 is free to move relative to dialator tube 46 it pulls cage 45, stretching cage 45, which is fixed at its opposite end at collar 41. As cage 45 stretches under this force, cage 45 lengthens and its diameter is reduced to the collapsed state allowing it to be inserted into a vessel.

Referring now again to FIG. 6, flexible membrane 58 is seen attached to cage 45. Membrane 58 can be formed of a number of plastics such as an elastomeric polyurethane or a silicone. It is preferred that membrane 58 be fluid impermeable. Also, those skilled in the art will recognize that the vessel occluders of the present invention are single use disposables. It has been found that membrane 58 may be attached to cage 45 using an adhesive; it is preferred that membrane 58 be attached only at its ends 60 and 62 to cage 45 and that membrane 58 be stretched somewhat onto cage 45 prior to gluing the ends 60 and 62 to cage 45. Membrane 58 will typically be only a few thousands of an inch in thickness. Again, preferably only the ends 60 and 62 of membrane 58 are attached to cage 45. As with the previous embodiment, all surfaces of vessel occluder 39, including membrane 58 are preferably treated to reduce the risk of providing a surface that collects blood cells or the like. Such treatment may take the form of a heparin coating.

In still another embodiment and referring now to FIG. 9 of the drawings, vessel occluder 64 is shown having catheter body 66 and inner tube 68 nested closely therein. Balloon cuff 70 is shown in the expanded state as inflated through inflation line 72. It will be appreciated that balloon cuff 70 is collapsed inside catheter body 66 prior to insertion of catheter body 66 into a principal vessel. When in the deployed state as shown in FIG. 9, cuff 70 has been pushed out of catheter body 66 axially by the movement of inner tube 68. When inflated cuff 70 defines passage 74 through which fluid can flow through the principal vessel. The cuff dimensions will be consistent with the teachings of this specification. That is, the outer dimensions of cuff 70 in the inflated state will be slightly larger than the lumen of the vessel into which it is deployed to ensure sufficient biasing force on the vessel walls to occlude tributary vessels. Materials and methods for making a balloon cuff 70 in accordance with the teachings herein will be well known to those of skill in the art. The operation of this embodiment will be essentially the same as described with the first embodiment described above. Also, as previously described catheter body 66 will be smaller in its outer dimension than the vessel lumen to permit blood to flow around catheter body 66 and through passage 74. All of the materials which will contact tissue in this embodiment will be made of biocompatible materials. Although not shown in FIG. 9, it may be suitable or desirable to include a dilator tip at the end of balloon cuff 70 to assist in percutaneous deployment.

It will be understood that in addition to occluding blood flow, such as retrograde flow, between a vessel and its tributaries, the present invention could be used in connection with aneurysms or dissections. In such cases, occluder 39 would not necessarily block tributary vessels. Occluder 39 would, however, function in a similar manner in that it allows blood flow through a vessel while isolating and preventing or limiting blood flow into the dissection or aneurysm. Accordingly it is contemplated that the present invention could be used in emergency surgeries to repair dissections or aneurysms while allowing blood perfusion of vital organs or limbs during surgical repair.

Prophetic Example

The vessel occlusion device is designed to allow for surgical procedures on vascular structures or adjacent organs while preserving prograde flow. This device is deployed into a vessel using the Seldinger technique. Briefly, an introducing needle is used to place a wire over which a dilator or series of dilators dilates a vessel allowing introduction of the device. This would allow the device to be used percutaneously. However, in instances when percutaneous approach is not necessitated, the device could be directly introduced into a vascular structure using an open surgical technique. Once this device is introduced to a lumen of said vascular structure, it is done so in its non-working (collapsed cage) configuration. That is, the device is introduced to the lumen with the membrane and support collapsed. The device is then deployed to the desired location. The location could be confirmed on ultrasound or other imaging technique. The device is positioned so that the most proximal aspect of the device is beyond the side branches of concern and the more distal end of the device are distal to the side branches of concern. In other words, the device is positioned within the lumen before the vasculature of concern and would extend axially along the lumen beyond the vasculature of concern. The device is deployed (expands) within the lumen of the vessel and adheres to the sidewall. The associated membrane covers the opening of and occludes the tributaries. One such application in a venous system would be vascular occlusion of the liver either in the setting of trauma or elective surgical procedure such as major hepatectomy for liver neoplasia. In this particular instance, a catheter could be inserted into the groin using a Seldinger technique via the femoral vein to advance to the level of the hepatic vein. Position is confirmed by imaging. The device is deployed so as to occlude the major hepatic veins. In-flow occlusion could be obtained using a simple surgical technique termed the Pringle maneuver. This combination of procedures would allow total vasculature isolation of the liver that could stop bleeding or allow for "bloodless" liver surgery. This device could similarly be deployed at the time of open surgical procedure. The catheter could be inserted directly in the vena cava. Other areas in which this device could potentially be efficacious would be in traumatic injuries to the liver and surgical procedures for patients with an aneurism or dissection of the aorta.

These procedures are not inclusive of all potential applications of the vessel occlusion device.

Many modifications and variations of the present invention are possible in light of the above teachings and may be practiced otherwise than as specifically described while within the scope of the appended claims. These antecedent recitations should be interpreted to cover any combination in which the inventive novelty exercises its utility.

What is claimed is:

1. A vessel occluder, comprising:
a catheter body defining a first internal passage;
a dilator closely received within said first internal passage;
a braided cage secured to said catheter body about a secured end and extending to a distal end to define a second internal passage extending between said ends;
said braided cage being movable between an expanded state and a collapsed state;
said dilator extending through said second internal passage;
a slip ring secured to said distal end of said cage and closely encircling an insertion end portion of said dilator;
a flexible membrane attached to only a central portion of said braided cage and spaced from said ends of said cage;
said dilator including a raised annular shoulder disposed at said insertion end portion and configured to seat against said slip ring;
an actuator knob linked to said dilator;
whereupon, said actuator knob is used to push said dilator through said catheter body such that said annular shoulder engages said slip ring to stretch said braided cage and said membrane to said collapsed state for insertion into a principal vessel and whereupon said actuator knob is used to release said cage to said expanded position to occlude with said membrane tributary vessels which would otherwise allow fluid to flow into said principal vessel and while still allowing fluid to flow through said braided cage at said ends through said principal vessel.

2. The vessel occluder as recited in claim 1, wherein the principal vessel has an inner diameter and said cage in said expanded state has an outer diameter being larger for applying a biasing force on the principal vessel to establish said occlusion of the tributary vessels.

3. The vessel occluder as recited in claim 1, wherein said membrane is attached to said cage only at opposite ends of said membrane.

4. The vessel occluder as recited in claim 3, wherein said membrane is attached to said cage by an adhesive.

5. The vessel occluder as recited in claim 1, wherein said braided cage is made of a plurality of braided nitinol strands that are set in the expanded state.

6. The vessel occluder as recited in claim 1 wherein all surfaces which contact fluid are treated with a coating of an anti-coagulation agent.

7. The vessel occluder as recited in claim 6, wherein said anticoagulation agent is heparin.

8. The vessel occluder as recited in claim 1, wherein said catheter and said dilator are formed of flexible plastic.

9. The vessel occluder as recited in claim 1, wherein said braided cage is made of stainless steel.

10. A vessel occluder as recited in claim 1, wherein said braided cage includes strands disposed in open mesh relationship for establishing said fluid flow through said ends of said braided cage.

* * * * *

UNITED STATES PATENT AND TRADEMARK OFFICE
CERTIFICATE OF CORRECTION

PATENT NO.         : 8,057,503 B2
APPLICATION NO.    : 12/019183
DATED              : November 15, 2011
INVENTOR(S)        : Timothy L. Fitzgerald et al.

It is certified that error appears in the above-identified patent and that said Letters Patent is hereby corrected as shown below:

Column 5, Line 61: "dialator" should read --dilator--.

Column 5, Line 62: "dialator" should read --dilator--.

Column 5, Line 64: "dialator" should read --dilator--.

Column 5, Line 65: "dialator" should read --dilator--.

Column 5, Line 65: "tube" should read --tube 46--.

Column 5, Line 67: "dialator" should read --dilator--.

Signed and Sealed this
Twenty-fourth Day of January, 2012

David J. Kappos
*Director of the United States Patent and Trademark Office*